United States Patent
Katoh et al.

(10) Patent No.: US 6,900,158 B2
(45) Date of Patent: May 31, 2005

(54) HIGH-MOLECULAR WEIGHT GEL AND DISPLAY DEVICE

(75) Inventors: Takashi Katoh, Kanagawa (JP); Akinori Fujita, Shizuoka (JP)

(73) Assignee: Fuji Photo Film Co., Ltd., Minami Ashigara (JP)

( * ) Notice: Subject to any disclaimer, the term of this patent is extended or adjusted under 35 U.S.C. 154(b) by 117 days.

(21) Appl. No.: 10/390,616

(22) Filed: Mar. 19, 2003

(65) Prior Publication Data

US 2003/0203817 A1 Oct. 30, 2003

(30) Foreign Application Priority Data

Mar. 19, 2002 (JP) ........................................ 2002-076550
May 16, 2002 (JP) ........................................ 2002-141738

(51) Int. Cl.$^7$ ............................................... B41M 5/30
(52) U.S. Cl. ........................ 503/218; 503/218; 503/220; 503/223
(58) Field of Search ................................. 503/200, 201, 503/214, 218, 220, 223

(56) References Cited

U.S. PATENT DOCUMENTS 6,120,588 A * 9/2000 Jacobson .................. 106/31.16
6,721,083 B2 * 4/2004 Jacobson et al. ........... 359/296

FOREIGN PATENT DOCUMENTS

| JP | 62-55967 | 3/1987 |
| JP | 9-160081 | 6/1997 |
| JP | 11-181031 | 7/1999 |
| JP | 11-236559 | 8/1999 |

* cited by examiner

*Primary Examiner*—B. Hamilton Hess
(74) *Attorney, Agent, or Firm*—Burns, Doane, Swecker & Mathis, L.L.P.

(57) ABSTRACT

A high-molecular weight gel having a leuco dye represented by the formula (L-1) as defined herein, connected thereto by covalent bond or single bond, and a high-molecular weight gel represented by the formula (R-1) as defined herein.

18 Claims, No Drawings

HIGH-MOLECULAR WEIGHT GEL AND DISPLAY DEVICE

FIELD OF THE INVENTION

The present invention relates to a high-molecular weight gel having an intramolecular ring-closure type leuco dye connected thereto by covalent bond and to a display device utilizing the high-molecular weight gel. Further, the invention relates to a high-molecular weight gel containing a repeating unit having a function to undergo reversible color development by stimulation, a repeating unit having a function to supply stimulation necessary for the color development, and a repeating unit having a function to form a high-molecular weight gel and to a display device utilizing the high-molecular weight gel.

BACKGROUND OF THE INVENTION

Papers capable of reversibly displaying digital information, which are so-called digital papers, are being actively studied at present because their importance will increase in the digital information era in the future. Representative examples of the mode include an electrophoresis display mode based on the movement of electrically charged fine particles, a thermally rewritable display mode utilizing the thermally reversible color development process of a leuco dye, and a mode utilizing the volume expansion of a high-molecular weight gel.

Among them, the thermally rewritable display mode utilizing the thermally reversible color development process of a leuco dye has been eagerly studied because white display on a basis of scatter close to paper can be utilized.

Leuco dyes are widely used as various display materials because they can realize a color development system by the acid-base reaction. For example, there are enumerated thermosensitive papers, pressure-sensitive papers, and thermosensitive printing materials. In addition, since the leuco dyes can realize a reversible color development system of the acid-base reaction, for example, reversible thermosensitive display materials comprising a combination of the leuco dye with a developer are known. The details of the reversible thermosensitive display materials are described in, for example, *Polymer Preprints*, Japan, Vol. 42, p. 736 (1993).

As the display material comprising a polymer having a leuco dye connected thereto by covalent bond are enumerated those disclosed in JP-A-11-181031. However, the display materials disclosed in this patent are of an irreversible color development system.

Further, as a display mode utilizing the phase change of a high-molecular weight gel are enumerated those disclosed in JP-A-11-236559 and JP-A-9-160081. However, the display materials disclosed in these patents still involve a problem such that the display contrast is low, and hence, its improvement has been demanded.

As the technology of complexing a high-molecular weight gel with a photo-functional material, high-molecular weight gels having a residue that can be ionically dissociated upon irradiation with light are disclosed in JP-A-62-55967. However, this residue involves a problem in stability of the chromophore, and hence, its improvement has been demanded.

As materials comprising a polymer having a leuco dye and a developer connected thereto by covalent bond are enumerated those disclosed in JP-A-11-181031. However, the materials disclosed in this patent relate to an irreversible display material comprising a combination with a functional group having an acid-proliferating function.

SUMMARY OF THE INVENTION

Under the circumstance of these problems, the invention has been made. A first object of the invention is to provide a novel high-molecular weight gel containing an intramolecular ring-closure type leuco dye and a display device having a high display performance by utilizing the high-molecular weight gel.

Further, a second object of the invention is to provide a display device having a high display performance by utilizing a combination of a group capable of undergoing reversible color development, a group for supplying stimulation necessary for the color development, and a high-molecular weight gel.

The foregoing objects of the invention have been solved by the following means.
(1) A high-molecular weight gel having a leuco dye represented by the following formula (L-1) connected thereto by covalent bond or single bond.

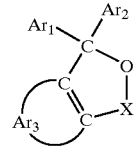

Formula (L-1)

In the formula, $Ar_1$ and $Ar_2$ each represents an aryl group or a heteroaryl group; $Ar_3$ represents an atomic group forming an aryl group or a heteroaryl group; and X represents CO or $SO_2$.
(2) The high-molecular weight gel as set forth in (1) as above, wherein the leuco dye represented by the formula (L-1) is a phthalide chromophore.
(3) The high-molecular weight gel as set forth in (1) or (2) as above, containing a repeating unit represented by the following formula (L-2) and a repeating unit represented by the following formula (L-3).

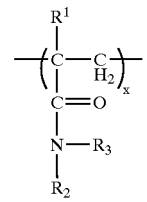

Formula (L-2)

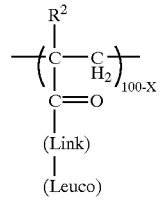

Formula (L-3)

In the formulae, Link represents a single bond or a divalent connecting group; Leuco represents the leuco dye represented by the formula (L-1), and either one of $Ar_1$ and $Ar_3$ in the formula (L-1) is connected to Link; $R_1$, $R_2$, $R_3$, and $R_4$ each represents a hydrogen atom or an alkyl group; and x represents mole %, and $0 \leq x < 100$.

(4) A high-molecular weight gel represented by the following formula (R-1).

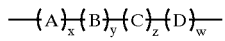
Formula (R-1)

In the formula, A represents a repeating unit having a function to undergo reversible color development by stimulation; B represents a repeating unit having a function to supply stimulation necessary for the color development; C represents a repeating unit having a function necessary for forming a high-molecular weight gel; D represents a crosslinking group-containing repeating unit; and x, y, z, and w each represents mole %, and $0.1 \leq x \leq 99.9$, $0.1 \leq y \leq 99.9$, $0 \leq z \leq 99.8$, $0 \leq w \leq 99.8$, and $(x+y+z+w)=100$.

(5) The high-molecular weight gel as set forth in (4) as above, wherein A is a partial structure represented by the following formula (R-2).

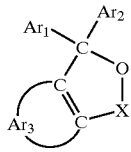
Formula (R-2)

In the formula, $Ar_1$ and $Ar_2$ each represents an aryl group or a heteroaryl group; $Ar_3$ represents an atomic group forming an aryl group or a heteroaryl group; and X represents CO or $SO_2$.

(6) The high-molecular weight gel as set forth in (4) or (5) as above, wherein B is a skeleton having a phenolic hydroxyl group.

(7) The high-molecular weight gel as set forth in any one of (4) to (6) as above, wherein A is a repeating unit represented by the following formula (R-3), and B is a repeating unit represented by the following general (R-4).

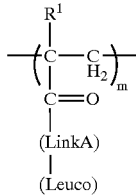
Formula (R-3)

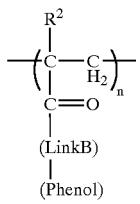
Formula (R-4)

In the formulae, LinkA and LinkB each represents a divalent connecting group; Leuco represents the leuco dye represented by the formula (R-2), and either one of $Ar_1$ and $Ar_3$ in the formula (R-2) is connected to LinkA; Phenol represents a skeleton having a phenolic hydroxyl group; $R^1$ and $R^2$ each represents a hydrogen atom or an alkyl group; and m and n each represents mole %, and $1 \leq m \leq 99$, and $1 \leq n \leq 99$.

(8) The high-molecular weight gel as set forth in any one of (4) to (7) as above, wherein C is a repeating unit comprising acrylic acid, an acrylic ester, acrylamide, or an N-alkyl acrylamide.

(9) A display device comprising a support having a layer containing the high-molecular weight gel as set forth in any one of (1) to (8) as above provided thereon.

DETAILED DESCRIPTION OF THE INVENTION

The invention will be described below in detail. Incidentally, in the specification, the numeral given before the term "to" means a minimum value, and the numeral given after the term "to" means a maximum value, respectively.

The high-molecular weight gel according to the invention is characterized in that it is connected to the leuco dye represented by the formula (L-1) by covalent bond.

The high-molecular weight gel that is used in the invention is defined such that it exhibits a state of a substance positioning in the middle of a solid and a liquid in which a solid as a high-molecular weight material and a liquid as a solvent are present jointly. Incidentally, in the specification, the term "(meth)" means the both of nomenclatures including "meth" and nomenclatures not including "meth". For example, the term "(meth)acrylamide derivative" means both a methacrylamide derivative and an acrylamide derivative.

While there are no particular limitations with respect to the high-molecular weight gel, examples include polymers, copolymers, crosslinked materials, and metal salts of, for example, (meth)acrylamide derivatives (such as acrylamide, methyl acrylamide, ethyl acrylamide, n-propyl acrylamide, isopropyl acrylamide, n-butyl acrylamide, t-butyl acrylamide, cyclohexyl acrylamide, benzyl acrylamide, hydroxymethyl acrylamide, methoxyethyl acrylamide, dimethylaminoethyl acrylamide, phenyl acrylamide, dimethyl acrylamide, diethyl acrylamide, β-cyanoethyl acrylamide, N-(2-acetoxyethyl) acrylamide, diacetone acrylamide, dimethylaminopropyl acrylamide, and methacrylamides corresponding to the foregoing acrylamides), hydroxyethyl (meth)acrylate, (meth)acrylic acid, maleic acid, vinylpyrrolidone, vinylpyridine, vinylsulfonic acid, vinylbenzenesulfonic acid, alkyl acrylates, styrene derivatives, vinyl carbazole derivatives, vinyl alcohol, and alkyl-substituted cellulose derivatives.

Preferred examples of the high-molecular weight gel that is used in the invention include polymers, copolymers, crosslinked materials, and metal salts comprising N-alkyl-substituted (meth)acrylaimides, poly(meth)acrylic acids, (meth)acrylamides, and vinylsulfonic acid, with polymers, copolymers, crosslinked materials, and metal salts comprising N-alkyl-substituted (meth)acrylaimides and poly(meth)acrylic acids being particularly preferred.

The high-molecular weight gel preferably has a molecular weight (number average molecular weight) in the range of from 1,000 to 1,000,000, and more preferably from 2,000 to 100,000. Further, the high-molecular weight gel may be in any state of a random copolymer, an alternating copolymer, or a block copolymer. Preferably, the high-molecular weight gel has a proper solids content concentration (gel concentration) in order to meet the performance as a display device.

As to the solvent of the high-molecular weight gel, various solvents can be properly used in order to meet the performance as a display device. Suitable examples include water, alcohols (such as methanol, ethanol, propanol, and butanol), halogenated hydrocarbons (such as chloroform, dichloromethane, and dichloroethane), aromatic hydrocarbons (such as benzene, toluene, and xylene), aliphatic hydrocarbons (such as hexane), ethers (such as diethyl ether and tetrahydrofuran), ketones (such as acetone and methyl ethyl ketone), esters (such as ethyl acetate), amides (such as dimethylformamide and dimethylacetamide), sulfoxides (such as dimethyl sulfoxide), and nitriles (such as acetonitrile and benzonitrile). Of these are preferable those having a high dielectric constant, such as water, alcohols, ketones, esters, amides, sulfoxides, and nitriles. Water and organic solvents such as acetone, tetrahydrofuran, and N,N-dimethylformamide are more preferred, with water being particularly preferred.

These solvents may be used singly or in admixture of two or more thereof, and any mixing ratio is employable for the mixed solvent.

An amount of the solvent to be contained in the high-molecular weight gel is not limited, but a ratio (mole ratio) of the solvent to the dry weight of the gel is preferably in the range of from 1:0.1 to 1:10,000, and more preferably from 1:1 to 1:1,000.

As to the introduction of the crosslinking structure, there are employable a method of irradiating a copolymer using a crosslinking precursor monomer such as N-hydroxymethyl acrylamide or an N-alkoxymethyl acrylamide with a heat, ultraviolet rays, or radiations; and a method of using a polyfunctional monomer (such as N,N'-methylenebis(meth)-acrylamide, bishydroxyethyl (meth)acrylate, and divinylbenzene).

A degree of crosslinking of the high-molecular weight gel is not limited, but the high-molecular weight gel is required to have a degree of crosslinking sufficient as a gel of a display device and to be properly crosslinked. A crosslinking density is preferably in the range of from 0 to 50 mole %, more preferably from 0 to 20 mole %, and most preferably from 0 to 10 mole %.

Next, the leuco dye represented by the formula (L-1) will be described. In the invention, the leuco dye represented by the formula (L-1) is synonymous with the leuco dye represented by the formula (R-2).

The leuco dye represented by the formula (L-1) can undergo color development by intramolecular ring-opening reaction and discoloration by intramolecular ring-closure reaction by giving stimulations such as acid-base, heat, pressure, electric field, magnetic field, and light. Preferably, the stimulation is an acid, a base, a heat, or an electric field. Examples of the leuco dye represented by the formula (L-1) include phthalide-based chromophores and fluoran-based chromophores. As to specific structural formulae of the respective chromophores, the phthalide-based chromophores are described on page 97 of *Chemistry and Applications of Leuco Dyes* (edited by R. Muthyala and published by Plenum Press, 1997), and the fluoran-based chromophores are described on page 159 of ibid. As the leuco dye represented by the formula (L-1) are preferred the phthalide-based chromophores.

In the formula (L-1), $Ar_1$ and $Ar_2$ each represents an aryl group or a heteroaryl group.

Examples of the aryl group include phenyl, 1-naphthyl, 2-naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, 4-dimethylaminophenyl, 4-diethylaminophenyl, 4-N-morpholinophenyl, and 4-dimethylamino-3-chlorophenyl; and examples of the heteroaryl group include 2-pyridyl, 5-methyl-2-pyridyl, 2-thienyl, 2-furyl, and 3-indolenyl. Further, the aryl group and the heteroaryl group may each have a substituent. As the substituent, the following substituent group V is enumerated.

Substituent Group V:

Alkylsilyl groups having from 1 to 30 carbon atoms, preferably from 2 to 20 carbon atoms, and more preferably from 3 to 10 carbon atoms (such as trimethylsilyl, triethylsilyl, tripropylsilyl, tributylsilyl, and tripentylsilyl); Halogen atoms (such as chlorine, bromine, iodine, and fluorine); Mercapto group; Cyano group; Carboxyl group; Phosphoryl group; Sulfo group; Hydroxyl group; Carbamoyl groups having from 1 to 10 carbon atoms, preferably from 2 to 8 carbon atoms, and more preferably from 2 to 5 carbon atoms (such as methylcarbamoyl, ethylcarbamoyl, and morpholinocarbamoyl); Sulfamoyl groups having from 0 to 10 carbon atoms, preferably from 2 to 8 carbon atoms, and more preferably from 2 to 5 carbon atoms (such as methylsulfamoyl, ethylsulfamoyl, and piperidinosulfamoyl); Nitro group; Alkoxy groups having from 1 to 20 carbon atoms, preferably from 1 to 10 carbon atoms, and more preferably from 1 to 8 carbon atoms (such as methoxy, ethoxy, 2-methoxyethoxy, and 2-phenylethoxy); Aryloxy groups having from 6 to 20 carbon atoms, preferably from 6 to 12 carbon atoms, and more preferably from 6 to 10 carbon atoms (such as phenoxy, p-methylphenoxy, p-chlorophenoxy, and 1-naphthoxy); Acyl groups having from 1 to 20 carbon atoms, preferably from 2 to 12 carbon atoms, and more preferably from 2 to 8 carbon atoms (such as acetyl, benzoyl, and trichloroacetyl); Acyloxy groups having from 1 to 20 carbon atoms, preferably from 2 to 12 carbon atoms, and more preferably from 2 to 8 carbon atoms (such as acetyloxy and benzoyloxy); Acylamino groups having from 1 to 20 carbon atoms, preferably from 2 to 12 carbon atoms, and more preferably from 2 to 8 carbon atoms (such as acetylamino); Sulfonyl groups having from 1 to 20 carbon atoms, preferably from 1 to 10 carbon atoms, and more preferably from 1 to 8 carbon atoms (such as methanesulfonyl, ethanesulfonyl, and benzenesulfonyl); Sulfinyl groups having from 1 to 20 carbon atoms, preferably from 1 to 10 carbon atoms, and more preferably from 1 to 8 carbon atoms (such as methanesulfinyl, ethanesulfinyl, and benzenesulfinyl); Amino group; Substituted amino groups having from 1 to 20 carbon atoms, preferably from 1 to 12 carbon atoms, and more preferably from 1 to 8 carbon atoms (such as methylamino, dimethylamino, benzylamino, anilino, diphenylamino, 4-methylphenylamine, 4-ethylphenylamino, 3-n-propylphenylamino, 4-n-propylphenylamino, 3-n-butylphenylamino, 4-n-butylphenylamino, 3-n-pentylphenylamino, 4-n-pentylphenylamino, 3-trifluoromethylphenylamino, 4-trifluoromethylphenylamino, 2-pyridylamino, 3-pyridylamino, 2-thiazolylamino, 2-oxazolylamino, N,N-methylphenylamino, and N,N-ethylphenylamino); Ammonium groups having from 0 to 15 carbon atoms, preferably from 3 to 10 carbon atoms, and more preferably from 3 to 6 carbon atoms (such as trimethylammonium and triethylammonium); Hydrazino groups having from 0 to 15 carbon atoms, preferably from 1 to 10 carbon atoms, and more preferably from 1 to 6 carbon atoms (such as a trimethylhydrazino group); Ureido groups having from 1 to 15 carbon atoms, preferably from 1 to 10 carbon atoms, and more preferably from 1 to 6 carbon atoms (such as a ureido group and an N,N-dimethylureido group); Imido groups having from 1 to 15 carbon atoms, preferably from 1 to 10 carbon atoms, and more preferably from 1 to 6 carbon atoms (such as a succimido group) Alkylthio groups having from 1 to 20 carbon atoms, preferably from 1 to 12 carbon atoms, and more preferably from 1 to 8 carbon atoms (such as methylthio, ethylthio, and propylthio); Arylthio groups having from 6 to 80 carbon atoms, preferably from 6 to 40 carbon atoms, and more preferably from 6 to 30 carbon atoms (such as phenylthio, p-methylphenylthio, p-chlorophenylthio, 2-pyridylthio, 1-naphthylthio, 2-naphthylthio, 4-propylcyclohexyl-4'-biphenylthio, 4-butylcyclohexyl-4'-biphenylthio, 4-pentylcyclohexyl-4'-biphenylthio, and 4-propylphenyl-2-ethynyl-4'-biphenylthio); Heteroarylthio groups having from 1 to 60 carbon atoms, preferably from 1 to 40 carbon atoms, and more preferably from 1 to 30 carbon atoms (such as 2-pyridylthio, 3-pyridylthio, 4-pyridylthio, 2-quinolylthio, 2-furylthio, and 2-pyrrolylthio); Alkoxycarbonyl groups having from 2 to 20 carbon atoms, preferably from 2 to 12 carbon atoms, and more preferably from 2 to 8 carbon atoms (such as methoxycarbonyl, ethoxycarbonyl, and 2-benzyloxycarbonyl); Aryloxycarbonyl groups having from 7 to 20 carbon atoms, preferably from 7 to 12 carbon atoms, and more preferably from 7 to 10 carbon atoms (such as phenoxycarbonyl); Unsubstituted alkyl groups having from 1 to 18 carbon atoms, preferably from 1 to 10 carbon atoms, and more preferably from 1 to 5 carbon atoms (such as methyl, ethyl, n-propyl, isopropyl, n-butyl, n-pentyl, and n-hexyl); Substituted alkyl groups having from 1 to 18 carbon atoms, preferably from 1 to 10 carbon atoms, and more preferably from 1 to 5 carbon atoms (such as hydroxymethyl, trifluoromethyl, benzyl, carboxyethyl, ethoxycarbonylmethyl, and acetylaminomethyl; and also including unsaturated hydrocarbon groups having from 2 to 18 carbon atoms, preferably from 3 to 10 carbon atoms, and more preferably from 3 to 5 carbon atoms (such as a vinyl group, an ethynyl group, a 1-cyclohexenyl group, a benzylidyne group, and a benzylidene group)); Substituted or unsubstituted aryl groups having from 6 to 20 carbon atoms, preferably from 6 to 15 carbon atoms, and more preferably from 6 to 10 carbon atoms (such as phenyl, naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, and 4-propylphenyl-2-ethynyl-4'-biphenyl); and Substituted or unsubstituted heteroaryl groups having from 1 to 20 carbon atoms, preferably from 2 to 10 carbon atoms, and more preferably from 4 to 6 carbon atoms (such as 3-pyridyl, 5-methyl-3-pyridyl, 2-thienyl, 2-furyl, morpholino, and tetrahydrofurfuryl).

The substituent group V may take a structure in which a benzene ring or a naphthalene ring is fused. In addition, these substituents may be further substituted with the substituent as described above for the substituent group V.

Preferred examples of the substituent include an alkyl group, an aryl group, an alkoxy group, an aryloxy group, an amino group, an alkylamino group, an arylamino group, a halogen atom, a hydroxyl group, and an alkoxycarbbnyl group.

$Ar_1$ and $Ar_2$ may be connected to each other to form a ring structure. The number of ring members to be formed is not particularly limited, but a 6-membered ring is preferred. In the case where a 6-membered ring is formed, a structure in which $Ar_1$ and $Ar_2$ are connected to each other via an oxygen atom or a sulfur atom is preferred.

$Ar_1$ and $Ar_2$ are each preferably a phenyl group, a naphthyl group, a pyridyl group, or an indolenyl group, and particularly preferably a phenyl group or an indolenyl group.

$Ar_3$ represents an atomic group forming an aryl group or a heteroaryl group. As the aryl group or the heteroaryl group are enumerated those as described above for $Ar_1$ and $Ar_2$. Preferred examples of the aryl group or the heteroaryl group formed by $Ar_3$ include a benzene ring, a naphthalene ring, and a pyridine ring, with a benzene ring and a pyridine ring being particularly preferred.

It is preferred that the high-molecular weight gel containing the formula (L-1) or the formula (R-2) as a partial structure has a structure in which either one of $Ar_1$ or $Ar_3$ is connected to Link or LinkA.

X represents CO or $SO_2$, and preferably CO.

Next, the formulae (L-2) and (L-3) will be described.

The divalent connecting group represented by Link is a single bond or comprises an atomic group constituted of a carbon atom, a nitrogen atom, a sulfur atom, or an oxygen atom. As the divalent connecting group are enumerated divalent connecting groups having from 0 to 60 carbon atoms, which are constituted of one or a combination of two or more of an alkylene group having from 1 to 20 carbon atoms (such as methylene, ethylene, propylene, butylene, pentylene, and cyclohexane-1,4-diyl), an alkenylene group having from 2 to 20 carbon atoms (such as ethenylene), an alkynylene group having from 2 to 20 carbon atoms (such as ethynylene), an amide group, an ether group, an ester group, a sulfonamide group, a sulfonic ester group, a ureido group, a sulfonyl group, a sulfinyl group, a thioether group, a carbonyl group, an —NR— group (wherein R represents a hydrogen atom, an alkyl group, or an aryl group), an arylene group having from 6 to 40 carbon atoms (such as 1,4-phenylene, 1,3-phenylene, 1,2-phenylene, 1,4-naphthylene, and 4,4'-biphenylene), a heteroarylene group having from 1 to 30 carbon atoms (such as pyridine-2,4-diyl, thiophene-2,4-diyl, and furan-2,4-diyl), an azo group, an azoxy group, and a heterocyclic divalent group (such as a piperazine-1,4-diyl group). These connecting groups may further have a substituent. As the substituent are enumerated those as described above for the substituent group V.

Link is preferably an alkylene group, an ether group-containing alkylene group, an ester group-containing alkylene group, or an amide group-containing alkylene group.

$R_1$, $R_2$, $R_3$, and $R_4$ each represents a hydrogen atom or an alkyl group. As the alkyl group are enumerated those as described above for the substituent group V.

$R_1$ and $R_4$ are each preferably a hydrogen atom or a methyl group.

Preferably, $R_2$ and $R_3$ are the same and represent a hydrogen atom; $R_2$ represents a hydrogen atom, and $R_3$ represents an unsubstituted alkyl group (such as a methyl group, an ethyl group, a propyl group, an isopropyl group, a butyl group, and a pentyl group); or $R_2$ and $R_3$ are the same and represent an unsubstituted alkyl group (such as a methyl group, an ethyl group, a propyl group, an isopropyl group, a butyl group, and a pentyl group).

The high-molecular weight gel represented by the formula (R-1) will be described below.

Formula (R-1)

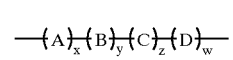

In the formula, A represents a repeating unit having a function to undergo reversible color development by stimulation; B represents a repeating unit having a function to supply stimulation necessary for the color development; C represents a repeating unit having a function necessary for forming a high-molecular weight gel; D represents a crosslinking group-containing repeating unit; and x, y, z, and w each represents mole %, and $0.1 \leq x \leq 99.9$, $0.1 \leq y \leq 99.9$, $0 \leq z \leq 99.8$, $0 \leq w \leq 99.8$, and $(x+y+z+w)=100$.

The repeating unit having a function to undergo reversible color development by stimulation, which is represented by A, will be described. As the stimulation are enumerated acid-base, heat, pressure, electric field, magnetic field, and light, with acid-base, heat, and electric field being preferred.

While there are no particular limitations with respect to the compound exhibiting reversible color development, compounds utilizing reversible conversion between a dye precursor called a leuco dye and a dye are preferable. Examples of the leuco dye include the chromophores as described in *Chemistry and Applications of Leuco Dyes* (edited by R. Muthyala and published by Plenum Press, 1997), specifically phthalide-based compounds, fluoran-based compounds, triarylmethane-based compounds, spiropyran-based compounds, triazene-based compounds, pyridine-based compounds, pyrazine-based compounds, phenothiazine-based compounds, leucoauramine-based compounds, and fluorene-based compounds, and preferably the phthalide-based chromophores are described on page 97 of *Chemistry and Applications of Leuco Dyes* (edited by R. Muthyala and published by Plenum Press, 1997), and the fluoran-based chromophores are described on page 159 of ibid.

Specific examples of the phthalide-based compounds include those disclosed in U.S. Pat. Nos. 3,491,111, 3,491,112, 3,491,116 and 3,509,174. Specific examples of the fluoran-based compounds include those disclosed in U.S. Pat. Nos. 3,624,107, 3,627,787, 3,641,011, 3,462,828, 3,681,390, 3,920,510 and 3,959,571. As the spiropyran-based compounds, those disclosed in U.S. Pat. No. 3,971,808 are enumerated. As the pyridine-based compounds and the pyrazine-based compounds, those disclosed in U.S. Pat. Nos. 3,775,424, 3,853,869 and 4,246,318 are enumerated.

The repeating unit having a function to supply stimulation necessary for the color development, which is represented by B, will be described. In the invention, there are no particular limitations with respect to the function to supply stimulation. But, preferred examples of the stimulation include an acid, a base, a heat, and light, with an acid being particularly preferred.

Examples of the compound having a function to supply an acid include phenol derivatives, salicyl derivatives, aromatic carboxylic acids, sulfonic acid derivatives, urea, thiourea, acid clay, bentonite, novolak resins, and metal complexes. Specific examples include those described in *Pulp and Paper Technology Times*, pp. 49–54 and pp. 65–70 (1985), JP-B-40-9309, JP-B-45-14039, JP-A-52-140483, JP-A-48-51510, JP-A-57-210886, JP-A-58-87089, JP-A-59-11286, and JP-A-60-176795.

The repeating unit represented by B is preferably a repeating unit obtained by polymerization of a polymerizable compound in which a functional site to supply stimulation and a polymerizable group are connected to each other by covalent bond. The polymerizable group is preferably a vinyl group.

The repeating unit having a function to form a high-molecular weight gel, which is represented by C, will be described. There are no particular limitations with respect to the repeating unit having a function to form a high-molecular weight gel. But, examples include repeating units obtained by polymerization of, for example, (meth)acrylamide derivatives (such as acrylamide, methyl acrylamide, ethyl acrylate, n-propyl acrylamide, isopropyl acrylamide, n-butyl acrylamide, t-butyl acrylamide, cyclohexyl acrylamide, benzyl acrylamide, hydroxymethyl acrylamide, methoxyethyl acrylamide, dimethylaminoethyl acrylamide, phenyl acrylamide, dimethyl acrylamide, diethyl acrylamide, β-cyanoethyl acrylamide, N-(2-acetoxyethyl)acrylamide, diacetone acrylamide, dimethylaminopropyl acrylamide, and methacrylamides corresponding to the foregoing acrylamides), hydroxyethyl (meth)acrylate, (meth)acrylic acid, maleic acid, vinylpyrrolidone, vinylpyridine, vinylsulfonic acid, vinylbenzenesulfonic acid, alkyl acrylates, styrene derivatives, vinyl carbazole derivatives, vinyl alcohol, or alkyl-substituted cellulose derivatives. Among them are preferable repeating units obtained by polymerization of N-alkyl-substituted (meth)acrylamides, poly(meth)acrylic acid, (meth)acrylates, (meth)acrylamides, or vinylsulfonic acid.

The crosslinking group-containing repeating unit, which is represented by D, will be described. There are no particular limitations with respect to the introduction of the crosslinking group. There are employable a method of irradiating a copolymer using a crosslinking precursor monomer such as N-hydroxymethyl acrylamide or an N-alkoxymethyl acrylamide with a heat, ultraviolet rays, or radiations; and a method of using a polyfunctional monomer (such as N,N'-methylenebis(meth)acrylamide, bishydroxyethyl (meth)acrylate, and divinylbenzene). Repeating units obtained by polymerization of a polyfunctional monomer are preferred.

x, y, z, and w each represents mole %, and $0.1 \leq x \leq 99.9$, $0.1 \leq y \leq 99.9$, $0 \leq z \leq 99.8$, $0 \leq w \leq 99.8$, and $(x+y+z+w)=100$. Any ratio of x to y can be employed, but a molar ratio of x to y is preferably in the range of from 1:0.1 to 1:100, and particularly preferably from 1:1 to 1:10. A molar ratio of x to z is preferably in the range of from 1:0.01 to 1:1,000, and particularly preferably from 1:1 to 1:100. w is preferably in the range of from 0 to 20, and particularly preferably from 0 to 10.

The formulae (R-3) and (R-4) will be described below. LinkA and LinkB each independently represents a single bond or a divalent connecting group. The divalent connecting group represented by LinkA and LinkB comprises an atomic group constituted of a carbon atom, a nitrogen atom, a sulfur atom, or an oxygen atom. As the divalent connecting group are enumerated divalent connecting groups having from 0 to 60 carbon atoms, which are constituted of one or a combination of two or more of an alkylene group having from 1 to 20 carbon atoms (such as methylene, ethylene, propylene, butylene, pentylene, and cyclohexane-1,4-diyl), an alkenylene group having from 2 to 20 carbon atoms (such as ethenylene), an alkynylene group having from 2 to 20 carbon atoms (such as ethynylene), an amide group, an ether group, an ester group, a sulfonamide group, a sulfonic ester group, a ureido group, a sulfonyl group, a sulfinyl group, a thioether group, a carbonyl group, an —NR— group (wherein R represents a hydrogen atom, an alkyl group, or an aryl group), an arylene group having from 6 to 40 carbon atoms (such as 1,4-phenylene, 1,3-phenylene, 1,2-phenylene, 1,4-naphthylene, and 4,4'-biphenylene), a heteroarylene group having from 1 to 30 carbon atoms (such as pyridine-2,4-diyl, thiophene-2,4-diyl, and furan-2,4-diyl), an azo group, an azoxy group, and a heterocyclic divalent group (such as a piperazine-1,4-diyl group). These connecting groups may further have a substituent. As the substituent are enumerated those as described above for the substituent group V.

LinkA and LinkB are preferably an alkylene group, an ether group-containing alkylene group, an ester group-containing alkylene group, or an amide group-containing alkylene group.

In the formulae (R-3) and (R-4), $R^1$ and $R^2$ each represents a hydrogen atom or an alkyl group. As the alkyl group are enumerated those as described above for the substituent group V.

In the formulae (R-3) and (R-4), $R^1$ and $R^2$ are each preferably a hydrogen atom or a methyl group.

The skeleton having a phenolic hydroxyl group, which is represented by B or Phenol, is a substituent-containing phenol. Preferred examples of the substituent-containing phenol include phenols substituted with a single substituent selected from any one of an alkyl, allyl, a halogen atom, a halo-substituted alkyl, a cycloalkyl, phenyl, a halo-substituted phenyl, an alkyl-substituted phenyl, biphenyl, benzyl, and an α-alkylbenzyl; phenols substituted with two or three substituents of the foregoing single substituents, provided that those substituted with two of the two or three substituents at the 2- and 6-positions are excluded; tetramethyl- or tetrahalo-substituted phenols; and phenols having a second hydroxyl group thereon, which are substituted with each of the foregoing substituents. Examples of the compound having a phenol skeleton include 2,2'-bis(4-hydroxyphenyl)propane, 4-t-butylphenol, 4-phenylphenol, 4-hydroxydiphenoxide, 1,1'-bis(3-chloro-4-hydroxyphenyl)cyclohexane, 1,1'-bis(4-hydroxyphenyl)cyclohexane, 1,1'-bis(3-chloro-4-hydroxyphenyl)-2-ethylbutane, 4,4'-sec-isooctylidenediphenol, 4,4'-sec-butylidenediphenol, 4-t-octylphenol, 4-p-methylphenylphenol, 4,4'-methylcyclohexylidenephenol, 4,4'-isopentylidenephenol, and benzyl p-hydroxybenzoate. Further, there are enumerated salicylic acid derivatives such as 4-pentadecylsalicylic acid, 3,5-di(α-methylbenzyl)salicic acid, 3,5-di(t-octyl)salicylic acid, 5-octadecylsalicylic acid, 5-α-(p-α-methylbenzylphenyl)ethylsalicylic acid, 3-α-methylbenzyl-5-t-octylsalicylic acid, 5-tetradecylsalicylic acid, 4-hexyloxysalicyclic acid, 4-cyclohexyloxysalicylic acid, 4-decyloxysalicylic acid, 4-dodecyloxysalicylic acid, 4-pentadecyloxysalicylic acid, and 4-octadecyloxysalicylic acid, and their zinc, aluminum, calcium, copper, and lead salts.

In the formulae (R-3) and (R-4), m and n each represents mole %, and $1 \leq m \leq 99$, and $1 \leq n \leq 99$. m is preferably in the range of from 1 to 50, and particularly preferably from 1 to 20. n is preferably in the range of from 1 to 70, and particularly preferably from 1 to 40. Any molar ratio of m to n can be employed, but a molar ratio of m to n is preferably from 1:05 to 1:20, and particularly preferably from 1:1 to 1:10.

There are no particular limitations with respect to the preparation process of the high-molecular weight gel according to the invention, but preferred examples include a process in which the high-molecular weight material is crosslinked simultaneously with its formation and a process in which the high-molecular weight material is crosslinked afterward. As the process in which the high-molecular weight material is crosslinked simultaneously with its formation, there can be utilized copolymerization of a variety of vinyl monomers with a crosslinkable monomer such as divinyl compounds, and polycondensation with a polyfunctional monomer. As the process in which the high-molecular weight material is crosslinked afterward, there can be utilized a process of exerting high-molecular weight materials having a different electric charge from each other to form an ion complex, a process of exerting the high-molecular weight compound and a crosslinking agent such as dialdehydes, dicarboxylic acids, and diepoxides, and crosslinking reaction by light or radiations. Specifically, reference can be made to the processes described in *Functional Gels* (Aizo Yamauchi, by Kyoritsu Shuppan Co., Ltd., 1990) and *Bases and Applications of Gel-Soft Materials* (Yoshihito Osada, by Sangyo Tosho Publishing Co., Ltd., 1991).

Specific examples of the high-molecular weight gel according to the invention will be given below, but it should not be construed that the invention is limited thereto. Incidentally, the term "solids content (%)" used hereunder means weight %.

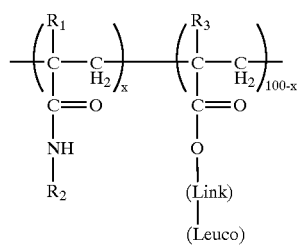

| No. | R1 | R2 | R3 | x* | Link | Leuco | Solvent | Solids content (%)** |
|---|---|---|---|---|---|---|---|---|
| 1-1 | H | H | H | 90 | (CH$_2$)$_6$ | | H$_2$O | 10 |

-continued

| No. | R₁ | R₂ | x | y | Link | Leuco | Solvent | Solids content** (%) |
|---|---|---|---|---|---|---|---|---|
| 1-2 | Me | H | Me | 80 | (CH₂)₂O(CH₂)₂ | (structure) | (structure) | 5 |
| 1-3 | H | i-Pr | H | 95 | (CH₂)₂O(C=O)(CH₂)₂ | (structure) | H₂O | 10 |

*x means mole %.
**The solids content (%) means mole % of the high-molecular weight material.
In Link, the left side represents a main chain side of the high-molecular weight material.
∼∼∼ shows the connecting position.

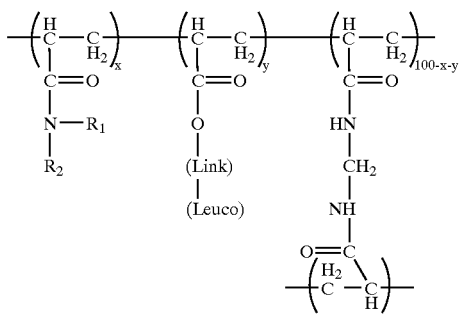

| No. | R₁ | R₂ | x | y | Link | Leuco | Solvent | Solids content** (%) |
|---|---|---|---|---|---|---|---|---|
| 1-4 | H | H | 80 | 15 | (CH₂)₆ | (structure) | H₂O | 30 |
| 1-5 | Et | Et | 75 | 20 | (CH₂)₂O(CH₂)₂ | (structure) | HCN(CH₃)₂ | 50 |

-continued
| | | | | | | | | |
|---|---|---|---|---|---|---|---|---|
| 1-6 | Me | Et | 85 | 10 | $(CH_2)_2CO_2(CH_2)_2$ | 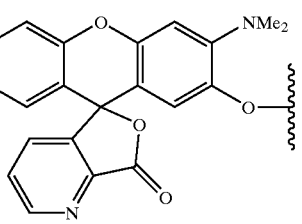 | $(CH_3)_2CO$ + $H_2O$ (1:1) | 10 |
1-7 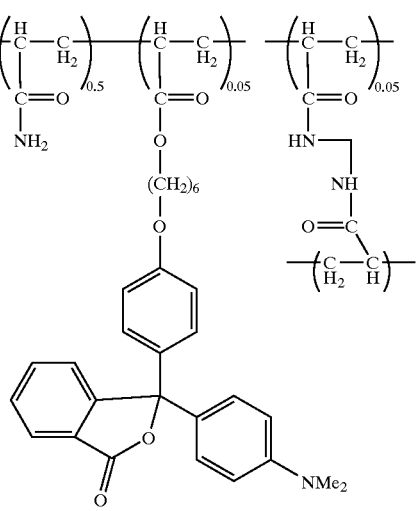 ($H_2O$) Solids content: 10%
1-8 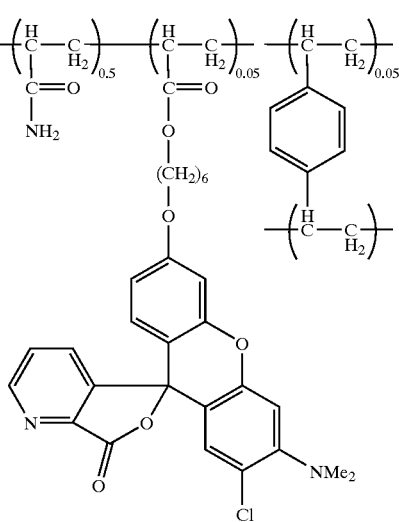 ($H_2O$ + $(CH_3)_2CO$) 1:1 Solids content: 13%

-continued
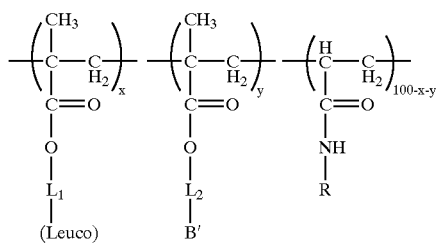
| No. | R | x | y | L₁ | Leuco | L₂ | B' | Solvent | Solids content (weight %) |
|---|---|---|---|---|---|---|---|---|---|
| 2-1 | H | 5 | 5 | (CH₂)₆ | | (CH₂)₆ | | H₂O | 20 |
| 2-2 | i-Pr | 10 | 20 | (CH₂)₂O(CH₂)₂ | | (CH₂)₄ | | THF | 30 |
| 2-3 | H | 5 | 15 | (CH₂)₂O(C=O)(CH₂)₂ | | (CH₂)₂O(CH₂)₂ | | DMF | 10 |
In L1 and L2, the left side represents a main chain side of the high-molecular weight material.
∼∼∼ shows the connecting position.

-continued

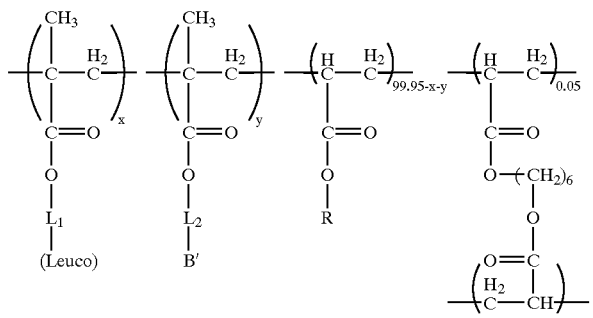

| No. | R | x | y | L₁ | Leuco | L₂ | B' | Solvent | Solids content (weight %) |
|---|---|---|---|---|---|---|---|---|---|
| 2-4 | H | 5 | 5 | (CH₂)₄ | (leuco structure with NMe₂ groups and CN) | (CH₂)₆ | (gallic acid ester structure) | H2O | 25 |
| 2-5 | o-Bu | 5 | 20 | (CH₂)₂O(CH₂)₂ | (xanthene/fluoran leuco structure with NMe₂ groups) | (CH₂)₄ | (phenoxy SO₃H structure) | THF + H2O | 30 |
| 2-6 | Et | 5 | 15 | (CH₂)₂O(C=O)(CH₂)₂ | (indole/spirolactone leuco structure with Et, NPr₂) | (CH₂)₆ | (chloro-hydroxybenzoate structure) | THF | 10 |

In L1 and L2, the left side represents a main chain side of the high-molecular weight material.

∿∿∿ shows the connecting position.

-continued

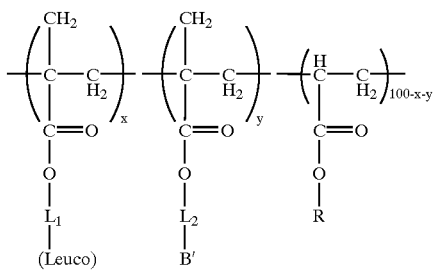

| No. | R | x | y | L₁ | Leuco | L₂ | B' | Solvent | Solids content (weight %) |
|---|---|---|---|---|---|---|---|---|---|
| 2-7 | Na | 6 | 18 | $(CH_2)_4$ | [leuco structure: triphenylmethanol with two NEt₂ groups and one O-linker] | $(CH_2)_2O(CH_2)_2$ | [3,4-dihydroxybenzoate] | H2O | 35 |
| 2-8 | Me | 4 | 20 | $(CH_2)_2O(CH_2)_2$ | [rhodamine-type leuco with MeNH and NMe₂, sulfone spirolactone] | $(CH_2)_4$ | [4-phosphonophenoxy] | acetone | 20 |
| 2-9 | Et | 5 | 15 | $(CH_2)_2O(C=O)(CH_2)_2$ | [indole-fused leuco with Et, O=CHN, NPr₂, pyridine lactone] | $(CH_2)_6$ | [3-chloro-4-hydroxybenzoate] | THF | 15 |

In L1 and L2, the left side represents a main chain side of the high-molecular weight material.

〜 shows the connecting position.

-continued

| No. | R | x | y | $L_1$ | Leuco | $L_2$ | B' | Solvent | Solids content (weight %) |
|---|---|---|---|---|---|---|---|---|---|
| 2-10 | Ph | 7 | 10 | $(CH_2)_2CONH(CH_2)_2$ | [leuco dye with $NEt_2$ group] | $(CH_2)_2O(CH_2)_2$ | [salicylate with $O_2C$, COO 1/2Zn, OH] | H2O | 40 |
| 2-11 | OBu | 5 | 15 | $(CH_2)_2O(CH_2)_2$ | [rhodamine-type leuco with $Ph_2N$, $CH_3$, NH] | $(CH_2)_4$ | [aromatic with $NHSO_2CH_3$, COO 1/2Zn] | H2O | 5 |
| 2-12 | OPh | 1 | 10 | $(CH_2)_2O(C=O)(CH_2)_2$ | [indole-fused leuco with Et, N, $NPr_2$] | $(CH_2)_6$ | [biphenyl with $O_2C$ and OH] | DMF | 25 |

In L1 and L2, the left side represents a main chain side of the high-molecular weight material.

∿∿∿ shows the connecting position.

-continued

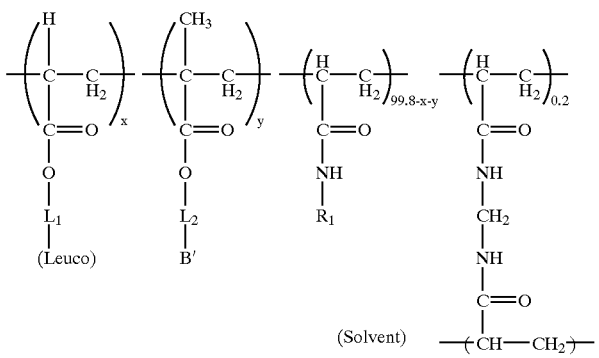

| No. | $L_1$ | Leuco | $L_2$ | B' | $R_1$ | Solvent | Solids content (weight %) |
|---|---|---|---|---|---|---|---|
| 2-13 | $(CH_2)_6$ | bis(4-dimethylaminophenyl)(4-)phenylmethanol with OH | $(CH_2)_4$ | 3,4-dihydroxyphenoxy | i-Pr | DMF | 5 |
| 2-14 | $(CH_2)_2O(CH_2)_2$ | bis(4-dimethylaminophenyl)(4-)phenylmethane with CN | $(CH_2)_6$ | 4-hydroxy-3-carboxyphenyl (COOH, OH) | sec-Bu | DMSO | 10 |
| 2-15 | $(CH_2)_2OC(=O)(CH_2)_2$ | spiropyran (1',3',3'-trimethyl-6-nitrospiro[2H-1-benzopyran-2,2'-indoline] derivative, N-C$_2$H$_5$, NO$_2$) | $(CH_2)_4$ | 3-chloro-4-hydroxyphenyl (Cl, OH) | CH$_3$ | DMF | 10 |

Next, the display device comprising the high-molecular weight gel having the leuco dye represented by the formula (L-1) connected thereto by covalent bond and the display device comprising the high-molecular weight gel represented by the formula (R-1) according to the invention will be described. The display device according to the invention is suitably used as, for example, display devices for displaying image information (such as image display devices).

While the configuration of the display device according to the invention includes configurations necessary for having functions as a display device, it may be one in which a layer containing the high-molecular weight gel is provided on a support, or one in which a layer containing the high-molecular weight gel is provided between a pair of substrates. Further, when an external light source is combined, it is possible to provide a display device having good contrast. As to the material quality of the display device, proper materials can be used.

That is, according the display device of the invention, it is possible to realize the desired image display by forming the state where the leuco dye causes intramolecular ring-opening by stimulation to undergo color development and the state where the leuco dye causes intramolecular ring-closure to become colorless according to the desired pattern. Especially, a method in which the color developed state is a state where the high-molecular weight gel is solvated and swollen in a solvent, and the colorless state is a state where the solvent in the high-molecular weight gel is released, and the high-molecular weight gel deposits from the solvent is preferred. In such a state, the color development is in a transparent colored state, and the colorless state is in a white state close to paper based on the scatter of the deposited high-molecular weight gel. Accordingly, a display device having good visibility can be provided.

While the display device according to the invention may be of either a reversible display or an irreversible display, it is preferably of a reversible display. There are no particular limitations with respect to a method of realizing the reversible color development. But, it is preferred to utilize a phase transition phenomenon on a basis of the temperature change of the high-molecular weight gel. Especially, it is known that in an aqueous solution of an N-alkyl acrylamide polymer, the polymer is in a dissolved state where water is solvated at low temperatures, whereas it is in a state where water is released from the high-molecular weight gel, and the high-molecular weight gel deposits at high temperatures. Accordingly, it is possible to use a combination of such phase change with the intramolecular ring-closure reaction of the leuco dye.

Besides the temperature change, it is possible to utilize pH change, electric field, adsorption and desorption of chemical substances such as surfactants, oxidation and reduction, and light as the stimulation to cause the phase transition of the high-molecular weight gel.

Preferably, the display device according to the invention utilizes the temperature as the stimulation.

Next, the display device comprising the high-molecular weight gel according to the invention will be described.

The display device according to the invention is achieved by complexing the function of the site A to reversibly form the state where the leuco dye causes intramolecular ring-opening by stimulation to undergo color development and the state where the leuco dye causes intramolecular ring-closure to become colorless; the function of the site B to supply stimulation necessary for the color development; and the function of the site C to form the high-molecular weight gel. That is, in the display device according to the invention, a reversible color development system is constructed by controlling a degree of the mutual action between the site A and the site B.

As the method of controlling the degree of the mutual action between the site A and the site B is preferable a method of changing a physical distance between the both. Specifically, it is preferred to utilize a swelling behavior of the high-molecular weight gel by the solvent. That is, the high-molecular weight gel exhibits a state of a substance positioning in the middle of a solid and a liquid in which a solid as a high-molecular weight material and a liquid as a solvent are present jointly and can change the amount of the solvent contained therein depending upon the stimulation.

As the representative stimulation are enumerated heat, pH, electric field, light, and change in solvent species, with heat, electric field, and change in solvent species being preferred.

In a method of changing the solvent species, since in a solvent incompatible with the high-molecular weight gel, the high-molecular weight gel does not contain the solvent, the distance between the site A and the site B becomes small, and the mutual action increases. Accordingly, the site A undergoes color development by the stimulation from the site B. On the other hand, since in a solvent compatible with the high-molecular weight gel, the solvent is incorporated into the high-molecular weight gel to cause swelling, the distance between the site A and the site B becomes large, and the mutual action decreases. Accordingly, the site A does not receive the stimulation from the site B to undergo discoloration. Thus, by causing the change of the mutual action reversibly at a desired position, it becomes possible to undergo the image display.

While the display device according to the invention may be of either a reversible display or an irreversible display, it is preferably of a reversible display. There are no particular limitations with respect to a method of realizing the reversible color development. But, it is preferred to utilize a difference in swelling properties on a basis of the change of the high-molecular weight gel by the change in solvent.

In the display device according to the invention, it is possible to realize full-color display by using a plurality of high-molecular weight gels having a leuco dye in a varied colored state, connected thereto.

The display device according to the invention can be utilized as light modulation materials for modulating the transmission amount of light, display devices for displaying images, temperature sensors for displaying the temperature, and sensors for detecting specific chemical substances.

Concretely, the devices as disclosed in JP-A-6-175165, JP-A-6-4021, JP-A-62-60690, JP-A-63-30279, JP-A-5-132640, JP-A-5-148442, and JP-A-6-341957 can be utilized.

EXAMPLES

The invention will be more specifically described below with reference to the Examples. The materials, reagents, substance amounts, and proportions thereof as shown in the Examples can be properly changed so far as they do not fall outside the scope of the invention. Accordingly, it should not be construed that the invention is limited to these specific examples.

Example 1

Synthesis of Compound (1–3) of the Invention

Synthesis of Compound M-1:

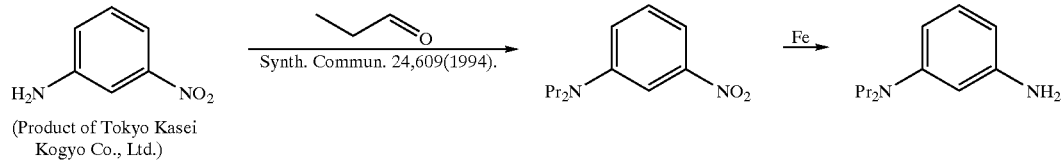

(Product of Tokyo Kasei Kogyo Co., Ltd.)

-continued

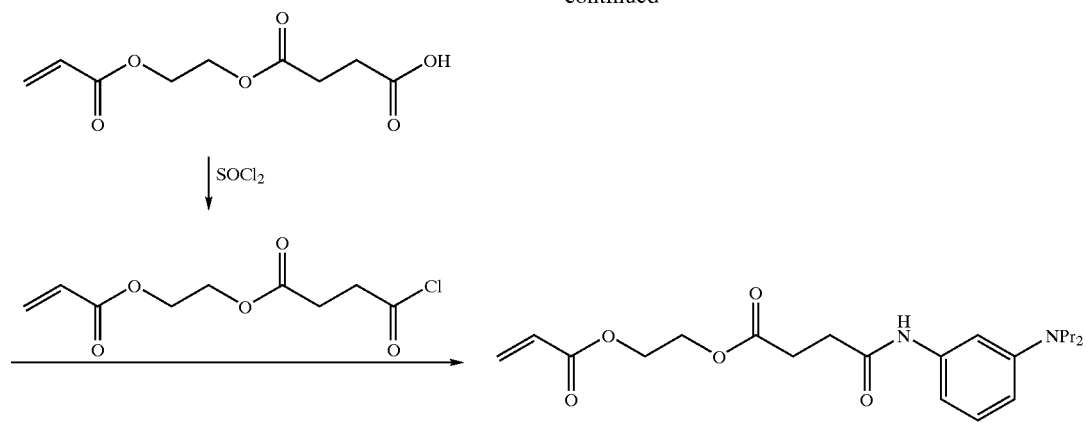

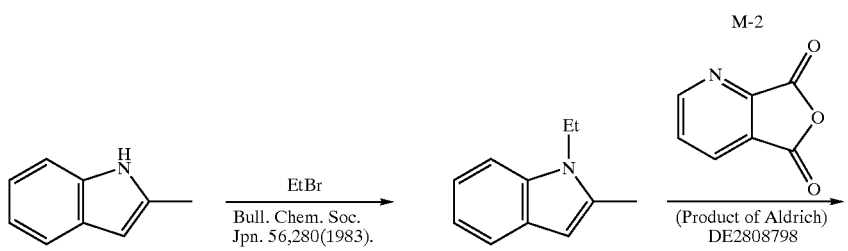

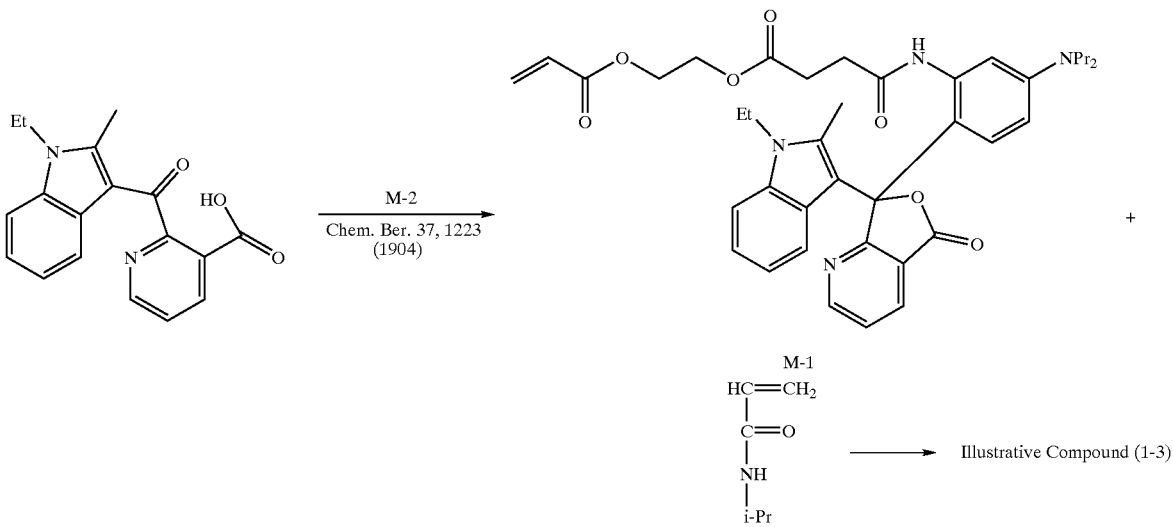

→ Illustrative Compound (1-3)

Compound (1–3) was synthesized according to the foregoing scheme. In a solution of 5.0 g of isopropylamide and 0.25 g of Compound (M-1) in 20 mL of tetrahydrofuran was added 50 mg of azobisisobutyronitrile (AIBN) as an initiator in a nitrogen atmosphere, and the mixture was allowed to react with stirring at 60° C. for 30 hours. The reaction mixture was poured into a large quantity of a hexane solution. A deposited high-molecular weight gel was filtered out, rinsed with hexane, and then dried to obtain Compound (1–3).

Yield: 3.8 g

White Powder

Number average molecular weight (Mn): 6,300 (measurement method: GPC, reduced as polystyrene)

Example 2

Display Device of the Invention

When 50 mg of Compound (1–3) of the invention was dissolved in 5 mL of water, the solution was transparent and colored blue. Next, when the aqueous solution was heated such that the inner temperature was 30° C. or higher, a high-molecular weight gel deposited, and the system became cloudy. When the reaction mixture was again cooled such that the inner temperature was 30° C. or lower, it returned to the original, transparent and blue state. The colored state was uniform from all angles, and the viewing-angle dependency was small different from liquid crystal displays. Namely, the reversible change between the transparent colored state and the cloudy state was observed by the change in temperature. This reversible color development system is based on a phenomenon in which since at lower temperatures, water is solvated in the high-molecular weight gel, the phthalide chromophore causes intramolecular ring-opening to undergo color development, whereas since at high temperatures, water is released from the high-molecular weight gel, and the high-molecular weight gel deposits, the phthalide chromophore causes intramolecular ring-closure to becomes cloudy.

Example 3

Synthesis of Illustrative Compound (2–6) of the Invention

Compound (M-2) was synthesized according to the foregoing scheme.

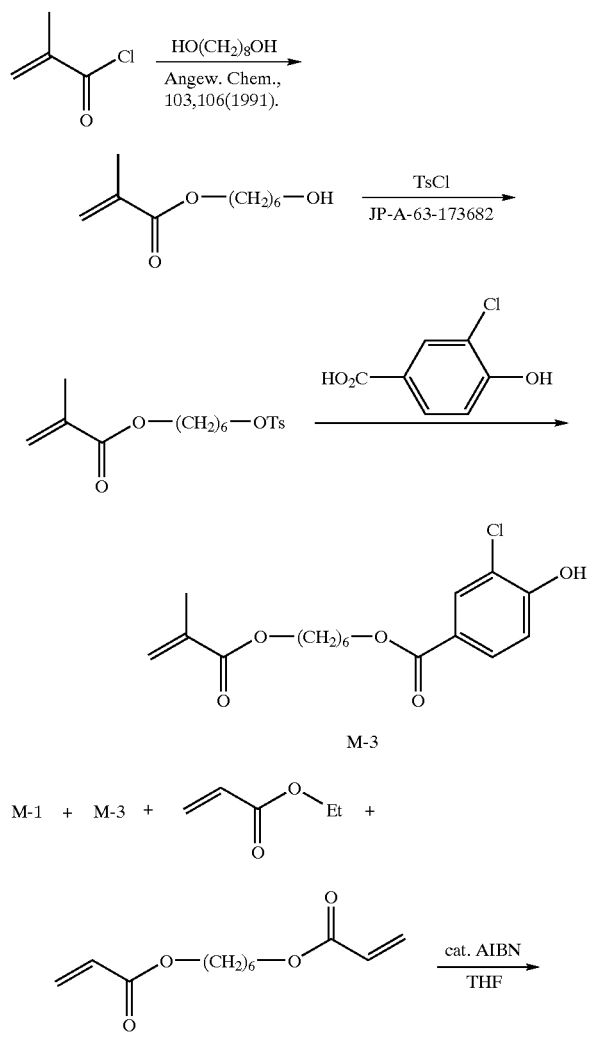

Synthesis of Illustrative Compound (2–6):

In a solution of 2.0 g of ethyl acrylate, 0.72 g of Compound (M-1), 2.4 g of Compound (M-3), and 0.2 g of Compound (M-4) (produced by Wako Pure Chemical Industries, Ltd.) in 20 mL of tetrahydrofuran was added 20 mg of azobisisobutyronitrile (AIBN) as an initiator in a nitrogen atmosphere, and the mixture was allowed to react with stirring at 60° C. for 12 hours. The reaction mixture was poured into a large quantity of a hexane solution, and a deposited solid was filtered out and rinsed with hexane. The obtained high-molecular weight material was dissolved in tetrahydrofuran (THF), to which was then added a large quantity of hexane, to obtain a deposited solid. This operation was repeated to obtain a solid, which was then dissolved in a THF solution. There was thus obtained Illustrative Compound (2–6) as the high-molecular weight gel of the invention.

Yield of solid: 3.2 g

Number average molecular weight of solid (Mn): 7,200 (GPC method, reduced as polystyrene)

Example 4

Display Device of the Invention

The THF solution of Illustrative Compound (2–6) of the invention is a colorless solution. Next, when this solution was added to a large quantity of hexane, a blue solid deposited. When this deposited blue solid was filtered out and again dissolved in a THF solution, the solution was again changed to a colorless solution. Namely, a reversible change between the colored state and the colorless state was observed depending upon the change in solvent. This reversible color development system by the change in solvent is based on a phenomenon where in the high-molecular weight gel state dissolved in THF, the THF molecule incorporated into the gel lowers the mutual action between the leuco dye site copolymerized in the gel and the phenol site as the developer, whereby the phthalide chromophore causes ring-closure to become colorless, whereas in the deposited state by the addition of hexane, the solvent in the high-molecular weight gel is turned out, and the mutual action between the leuco dye site copolymerized in the gel and the phenol site as the developer increases, whereby the phthalide chromophore causes ring-opening to become a color developed state.

Next, when Illustrative Compound (2–6) of the invention was applied on PET to form a film and thoroughly dried, the film became a state where the whole was color developed blue.

Next, when a THF solution was dropped on a desired position, it was observed that only the site at which the THF solution was dropped became colorless.

By using the high-molecular weight gel according to the invention, it is possible to cause a reversible change between the transparent colored state and the cloudy state on a basis of the change in temperature and to provide a display device that can be readily made large in area, is small in viewing-angle dependency and is low in product cost.

In addition, by using the high-molecular weight gel according to the invention, it is possible to cause a reversible change between the colored state and the colorless state on a basis of the change in solvent and to efficiently provide a reversible display device that can be readily made large in area, is good in visibility and is low in product cost.

This application is based on Japanese Patent application JP 2002-141738, filed May 16, 2002, the entire content of which is hereby incorporated by reference, the same as if set forth at length.

What is claimed is:

1. A display device comprising a support and a layer containing a gel having a leuco dye represented by formula (L-1):

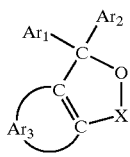
(L-1)

wherein $Ar_1$ and $Ar_2$ each represents an aryl group or a heteroaryl group; $Ar_3$ represents an atomic group forming an aryl group or a heteroaryl group; and X represents CO or $SO_2$, connected thereto by covalent bond or single bond, and the gel has color development or discoloration by giving stimulations of changing temperature or changing solvent species.

2. The display device of claim 1, wherein each of $Ar_1$ and $Ar_2$ is selected from the group consisting of phenyl, 1-naphthyl, 2-naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, 4-dimethylaminophenyl, 4-diethylaminophenyl, 4-N-morpholinophenyl, 4-dimethylamino-3-chlorophenyl, 2-pyridyl, 5-methyl-2-pyridyl, 2-thienyl, 2-furyl, and 3-indolenyl.

3. The display device of claim 1, wherein each of $Ar_1$ and $Ar_2$ is selected from the group consisting of a phenyl group, a naphthyl group, a pyridyl group, and an indolenyl group.

4. The display device of claim 1, wherein each of $Ar_1$ and $Ar_2$ is selected from the group consisting of a phenyl group and an indolenyl group.

5. The display device of claim 1, wherein $Ar_3$ is selected from the group consisting of phenyl, 1-naphthyl, 2-naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, 4-dimethylaminophenyl, 4-diethylaminophenyl, 4-N-morpholinophenyl, 4-dimethylamino-3-chlorophenyl, 2-pyridyl, 5-methyl-2-pyridyl, 2-thienyl, 2-furyl, and 3-indolenyl.

6. The display device of claim 1, wherein $Ar_3$ is selected from the group consisting of a phenyl group, a naphthyl group, a pyridyl group, and an indolenyl group.

7. The display device of claim 1, wherein $Ar_3$ is selected from the group consisting of a phenyl group and an indolenyl group.

8. The display device of claim 1, wherein $Ar_3$ is selected from the group consisting of a benzene ring, a naphthalene ring, and a pyridine ring.

9. The display device of claim 1, wherein the leuco dye comprises a phthalide chromophore.

10. The display device of claim 1, wherein the gel comprises a repeating unit represented by formula (L-2) and a repeating unit represented by formula (L-3):

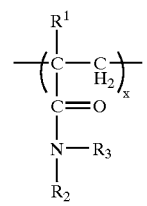
(L-2)

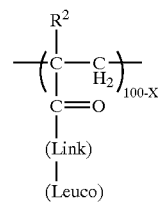
(L-3)

wherein Link represents a single bond or a divalent connecting group; Leuco represents the leuco dye represented by the formula (L-1), and either on of $Ar_1$ and $Ar_3$ in the formula (L-1) is connected to Link; $R_1$, $R_2$, $R_3$, and $R_4$ each represents a hydrogen atom or an alkyl group; and x represents mole %, and $0 \leq x < 100$.

11. The display device of claim 1, the gel having a number average molecular weight of from 1,000 to 1,000,000.

12. The display device of claim 1, the gel having a crosslinking density of from 0 to 50 mole %.

13. The display device of claim 1, wherein the gel is represented by formula (R-1):

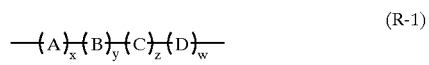
(R-1)

wherein B represents a repeating unit having a function to supply stimulation necessary for the color development; C represents a repeating unit having a function necessary for forming a high-molecular weight gel; D represents a crosslinking group-containing repeating unit; x, y, z, and w each represents mole %, and $0.1 \leq x \leq 99.9$, $0.1 \leq y \leq 99.9$, $0 \leq z \leq 99.8$, $0 \leq w \leq 99.8$, and $(x+y+z+w)=100$; and A is a partial structure represented by formula (L-1):

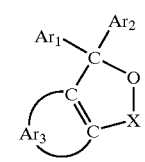
(L-1)

wherein $Ar_1$ and $Ar_2$ each represents an aryl group or a heteroaryl group; $Ar_3$ represents an atomic group forming an aryl group or a heteroaryl group; and X represents CO or $SO_2$.

14. The display device of claim 13, wherein B is a skeleton having a phenolic hydroxyl group.

15. The display device of claim 13, wherein A is a repeating unit represented by formula (R-3), and B is a repeating unit represented by formula (R-4):

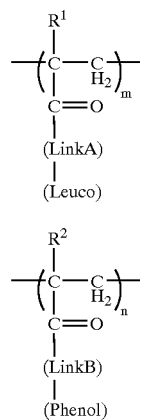

(R-3)

(R-4)

wherein LinkA and LinkB each represents a divalent connecting group; Leuco represents the leuco dye represented by the formula (L-1) and either one of $Ar_1$ and $Ar_3$ in the formula (L-1) is connected to LinkA; Phenol represents a skeleton having a phenolic hydroxyl group; $R^1$ and $R^2$ each represents a hydrogen atom or an alkyl group and m and n each represents mole %, and $1 \leq m \leq 99$, and $1 \leq n \leq 99$.

16. The display device of claim 13, wherein C is a repeating unit comprising acrylic acid, an acrylic ester, acrylamide, or an N-alkyl acrylamide.

17. The display device of claim 13, the gel having a number average molecular weight of from 1,000 to 1,000,000.

18. The display device of claim 10, wherein x is from 50 to 99.

* * * * *